(12) United States Patent
Lim et al.

(10) Patent No.: US 10,485,818 B2
(45) Date of Patent: Nov. 26, 2019

(54) DIETARY FIBRE COMPOSITION

(71) Applicant: InQpharm Group Sdn Bhd, Kuala Lumpur (MY)

(72) Inventors: Yee Mae Lim, Kuala Lumpur (MY); Pui Ee Wong, Kuala Lumpur (MY); Min Pau Tan, Kuala Lumpur (MY)

(73) Assignee: INQPHARM GROUP SDN BHD, Kuala Lumpur (MY)

( * ) Notice: Subject to any disclaimer, the term of this patent is extended or adjusted under 35 U.S.C. 154(b) by 0 days.

(21) Appl. No.: 15/529,818

(22) PCT Filed: Nov. 26, 2015

(86) PCT No.: PCT/MY2015/000099
§ 371 (c)(1),
(2) Date: May 25, 2017

(87) PCT Pub. No.: WO2016/085322
PCT Pub. Date: Jun. 2, 2015

(65) Prior Publication Data
US 2017/0319616 A1    Nov. 9, 2017

(30) Foreign Application Priority Data
Nov. 26, 2014 (MY) .......................... PI2014703525

(51) Int. Cl.

| | |
|---|---|
| *A61K 31/736* | (2006.01) |
| *A23L 29/244* | (2016.01) |
| *A23L 29/256* | (2016.01) |
| *A23L 29/269* | (2016.01) |
| *A23L 33/00* | (2016.01) |
| *A23L 33/21* | (2016.01) |
| *A61K 31/723* | (2006.01) |
| *A61K 31/731* | (2006.01) |
| *A23L 33/10* | (2016.01) |
| *A23L 2/52* | (2006.01) |

(52) U.S. Cl.
CPC .............. *A61K 31/736* (2013.01); *A23L 2/52* (2013.01); *A23L 29/244* (2016.08); *A23L 29/256* (2016.08); *A23L 29/27* (2016.08); *A23L 33/10* (2016.08); *A23L 33/21* (2016.08); *A23L 33/30* (2016.08); *A61K 31/723* (2013.01); *A61K 31/731* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,410,660 B2 * | 8/2008 | Mercati ................... | A23L 33/24 424/725 |
| 2005/0020535 A1 * | 1/2005 | Vuksan .................... | A21D 2/18 514/54 |
| 2006/0228397 A1 | 10/2006 | Gahler et al. | |
| 2011/0223192 A1 * | 9/2011 | Gahler ................. | A61K 31/736 424/195.18 |
| 2013/0085571 A1 * | 4/2013 | Mueller .................. | A61L 27/20 623/15.12 |
| 2013/0295263 A1 * | 11/2013 | Popp ..................... | A23L 1/0522 426/575 |

FOREIGN PATENT DOCUMENTS

| | | |
|---|---|---|
| JP | 2011-004702 A | 6/2009 |
| JP | 2010-254702 A | 11/2010 |
| JP | WO2012/086593 A1 | 6/2012 |
| JP | WO2011/074670 A1 | 12/2014 |
| KR | 101367741 B1 * | 2/2014 ............... A23L 1/06 |
| WO | 2013142482 A1 | 9/2013 |
| WO | WO-2013142482 A1 * | 9/2013 ............. A61K 45/06 |

OTHER PUBLICATIONS

Subject Matter Eligibility Examples: Life Sciences (May 2016) (Year: 2016).*
Parry (2010) "Konjac glucomannan," Food Stabilisers, Thickeners and Gelling Agents. 1:198-217.
Takigami et al. (2009) "Konjac Mannan," Handbook of Hydrocolloids. 1:889-901.
International Search Report corresponding to International Patent Application No. PCT/MY2015/000099, dated Mar. 10, 2016.
Jean-Marc Parry: "Konjac Glucomannan," in "Food Stabilisers, Thickeners and Gelling Agents," Chapter 11, Wiley-Blackwell, Oxford, UK (Nov. 6, 2009).

* cited by examiner

*Primary Examiner* — Dale R Miller
(74) *Attorney, Agent, or Firm* — Lathrop Gage LLP; James H. Velema, Esq.

(57) ABSTRACT

The invention provides a composition comprising glucomannan, carrageenan, xanthan gum and a monovalent or divalent cation salt. The composition is suitable for use in managing weight, combating obesity, combating metabolic syndrome, promoting satiety, reducing appetite, combating diabetes, lowering blood cholesterol, lowering blood pressure, reducing postpranial glycaemia, or increasing insulin sensitivity.

26 Claims, 1 Drawing Sheet

DIETARY FIBRE COMPOSITION

RELATED APPLICATIONS

This application is a 35 U.S.C. § 371 filing of International Application No. PCT/MY2015/000099, filed Nov. 26, 2015, which claims priority to Malaysian Patent Application No. PI2014703525, filed Nov. 26, 2014, each of which is incorporated herein by reference in its entirety.

TECHNICAL FIELD OF THE INVENTION

The present invention relates to a dietary fibre composition. More particularly, the present invention relates to a composition for use in reducing appetite, promoting satiety, as well as treating or preventing obesity and/or for treating or preventing metabolic diseases, such as metabolic syndrome.

BACKGROUND OF THE INVENTION

The listing or discussion of an apparently prior-published document in this specification should not necessarily be taken as an acknowledgement that the document is part of the state of the art or is common general knowledge.

Obesity is a medical condition that is increasingly prevalent in the global population. It occurs when a person having body fat that has accumulated in excess possibly causes an adverse effect on health. The accumulated fat in the body of an obese person plays a significant role in the pathogenesis of various diseases, including diabetes, hypertension, coronary heart diseases, and various types of cardiovascular-related metabolic syndrome. Therefore, body weight management has become a key element of modern healthcare.

Obesity and excess body weight can result from a high level of energy intake that exceeds the body's energy expenditure, which may be caused by overeating, inactive or sedative lifestyle, genetics or family history, medical conditions and/or other factors. In order to combat or prevent obesity or excess body weight, lifestyle changes could be one of the main solutions. However, as lifestyle changes may be difficult to implement and physical activity in the developed world continues to decline, control of calorie intake has become a more accommodating and effective way to prevent the further increase of the prevalence of worldwide obesity and its associated health problems.

Reduction of total caloric intake from diet could be achieved via diet planning, which includes reduction of amount of diet intake or ingestion of drugs or supplements such as caloric blocker, meal replacement, appetite reducer and others. However, the effectiveness of currently available drugs and supplements for promoting weight control or weight loss is very variable, particularly if they are not used in conjunction with a calorie-restricted diet and exercise regimen.

There have been a few existing technologies described in the prior art related to compositions for promoting or inducing the sensation of satiety as a means of suppressing of appetite. In this regard, it is known in the art that the viscosity, swelling and gel forming physiochemical properties of dietary fibre could be associated with the prolonged gastric emptying, increased gastric distention and satiety, and attenuated postpranial glycaemia.

For example, U.S. Pat. No. 7,410,660 describes pharmaceutical, nutraceutical, dietetic and nutritional compositions based on vegetable fibres. The compositions comprise glucomannan, *Opuntia ficus indica* and microcrystalline cellulose, and are said to present a high gastrointestinal swelling index that induces an immediate feeling of fullness, release of cholecystokinins and slowing of gastric voiding which prolongs the feeling of fullness. Associating the complex of three vegetable fibres with a mixture of freeze-dried mucilages (1-10% by weight of composition) is also said to increase its gastrointestinal swelling properties. However, the swelling index of the composition of U.S. Pat. No. 7,410,660 was shown to be synergistically increased under neutral conditions, not under the conditions that resemble those found at the intended site of action, namely the stomach.

Takigami et al (2009) (Handbook of Hydrocolloids, pp 889-901, Woodhead Publishing Ltd) describes how glucomannan exhibits a synergistic interaction with either of xanthan gum or kappa-carrageenan. Due to the synergism arising from two fibres, the viscosity and gel strength of the mixture of glucomannan and either of kappa-carrageenan or xanthan gum are several times higher than the inherent viscosity and gel strength of the individual fibres. The synergism is said to be dependent on several factors including the ratio of the mixture, ionic strength and pH of the solution. Maximum viscosity was observed at a ratio of 80:20 for both a mixture of glucomannan and kappa-carrageenan or xanthan gum, whereas the maximum gel strength occurred at a ratio of 40:60 for both mixtures. However, there is no mention of a composition containing potassium salts. It is shown in Takigami, 2009 that the viscosity of glucomannan is decreased with decreasing of pH value. However, there is no disclosure in this prior art on any combination of the dietary fibres for use in appetite reducing or weight management that provides good swelling, viscosity and gelling effects.

In view of the existing compositions for appetite reducing or satiety inducing available in the field which do not provide the desired physiochemical properties that increase their effectiveness as an appetite reducer or satiety inducer to control body weight and/or treating obesity, and related disorders, such as metabolic syndrome, it is therefore an on-going need for the industry to have a unique and optimum composition with innovative combination of ingredients that shows synergistic physiochemical properties, particularly swelling, viscosity and gelling effect to overcome the drawbacks of the existing technologies.

SUMMARY OF THE INVENTION

An object of the present invention is to provide a composition containing a unique combination of active ingredients that shows synergistic physiochemical properties, particularly swelling, viscosity and gelling effect, which is adapted for promoting satiety or fullness; reducing appetite, hunger sensation or food craving, which is directly or indirectly correlated with the management and control of body weight, prevention or treatment of obesity as well as its associated metabolic syndromes.

The preceding object is met, in whole or in part, by one or more of the embodiments of the present invention, in which one of the embodiments discloses a dietary fibre composition comprising glucomannan; carrageenan; xanthan gum; and a monovalent/divalent cation salt.

According to a preferred embodiment of the present invention, the glucomannan is konjac glucomannan. Preferably, it is present in an amount of 30-50% w/w by weight of the composition.

In accordance with another preferred embodiment of the present invention, the carrageenan is derived from a red algae, which is preferably selected from the group consisting of Gigartinaceae; Solieriaceae; Hypneaceae; and Furcellariaceae.

The carrageenan is preferably kappa-carrageenan. It is preferable that the carrageenan is present in an amount of 15-25% w/w by weight of the composition.

Still another preferred embodiment of the present invention discloses that the xanthan gum is present in an amount of 10-25% w/w by weight of the composition.

Yet another preferred embodiment of the present invention discloses that the monovalent/divalent cation salt is a potassium salt, which is preferably a water-soluble potassium salt. Most preferably, the potassium salt is selected from the group consisting of potassium bicarbonate, potassium chloride, potassium acetate, potassium phosphate and potassium citrate. Preferably, the potassium salt is present in an amount of 10-30% w/w by weight of the composition.

In accordance with another preferred embodiment of the present invention, it is disclosed that the composition comprises 40% w/w glucomannan; 24% w/w carrageenan; 16% w/w xanthan gum; and 20% w/w monovalent/divalent cation salt.

Still another preferred embodiment of the present invention discloses that the composition swells, increases viscosity and gels under gastric and intestinal conditions.

The composition as described in one of the preferred embodiments of the present invention is preferably in the form of a capsule. Preferably, the composition is a food product or beverage product such as a dietary supplement, a health supplement or a food additive.

A further embodiment of the present invention discloses a dietary fibre composition which further comprises a therapeutic agent, such as an absorption altering agent, an appetite altering agent, a metabolism altering agent, a cholesterol lowering agent or any combination thereof.

Another embodiment of the present invention is a pharmaceutical composition comprising a composition as described in the foregoing embodiments, and a pharmaceutically acceptable carrier and/or excipient and/or diluent.

Another further embodiment of the present invention is a composition comprising glucomannan; carrageenan; xanthan gum; and a potassium salt, for use in promoting satiety, reducing appetite, managing weight, combating obesity, managing blood glucose level, combating diabetes, lowering blood cholesterol, or combating metabolic syndrome.

Yet another embodiment of the present invention is a method of promoting satiety, reducing appetite, managing weight, combating obesity, managing blood glucose level, combating diabetes, lowering blood cholesterol, or combating metabolic syndrome, wherein the method comprising administering to a subject a composition comprising glucomannan; carrageenan; xanthan gum; and a monovalent/divalent cation salt. Preferably, the composition is administered to the subject between about 10 minutes and 120 minutes before or after a meal, such as between 60 minutes and 30 minutes before or after a meal, or any time between two meals.

The composition as embodied in the present invention is capable of providing a composition with active ingredients that act synergistically to form a highly swellable, viscous, thick and indigestible gel structure under gastric or intestinal conditions. This physical structure increases the volume of gastric content and slows down the rate at which food leaves the stomach to the duodenum, thereby inducing the feeling of satiety or fullness. Hence, a composition comprising these four active ingredients is expected to induce weight loss by enhancing the feeling of fullness, which subsequently reduces appetite or hunger sensation and intake of calories.

One skilled in the art will readily appreciate that the present invention is well adapted to carry out the objects and obtain the ends and advantages mentioned, as well as those inherent therein. The embodiments described herein are not intended as limitations on the scope of the invention.

DETAILED DESCRIPTION OF THE INVENTION

Hereinafter, the invention shall be described according to preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claim.

Accordingly, a first aspect of the invention provides a composition comprising: glucomannan; carrageenan; xanthan gum; and a monovalent/divalent cation salt. It is appreciated that the composition may be called a dietary fibre composition.

In one embodiment, the composition of the invention consists essentially of glucomannan; carrageenan; xanthan gum; and a monovalent/divalent cation salt. However, it will be appreciated that it may be desirable to incorporate further components into the composition. For example, as will become clear below, the composition may be part of a food product or beverage product and/or may further comprise one or more additional therapeutic agents such as an absorption altering agent, an appetite altering agent, a metabolism altering agent, a cholesterol lowering agent or any combination thereof.

Glucomannans are neutral polysaccharides produced by many plants where they serve as energy reserves and in some cases structural roles. The polysaccharides comprise, in most cases, predominantly mannose residues with glucose as the second sugar. The polysaccharides may contain some acetylated residues, and may contain some galactose side chains.

Glucomannans can be isolated from a variety of natural sources including eastern white pine (*Pinus strobes*), higanbana (*Lycoris radiata*), konjac (*Amorphophallus konjac*), lily (*Lilium auratum*), orchid (*Tubera salep*), ramie (*Boehmeria nivea*), and redwood (*Sequois sempervirens*). All such glucomannans are included in the scope of the present invention, although it is preferred that the glucomannan is sourced from konjac. Ratios of mannose to glucose in glucomannan typically range from 1.5 to 4.2, and the molecular weight of glucomannan can range from 500,000 to 2,000,000 daltons. It is known in the art that different sources of glucomannan may elicit different physiochemical properties.

Most commonly, glucomannan is isolated from konjac root. Konjac glucomannan is a polysaccharide extracted from the *Amorphophallus konjac* plant (or group of plants) which is, itself, a member of the Araceae family.

Thus, in a particular and preferred embodiment of the invention, the glucomannan is konjac glucomannan.

Konjac glucomannans are high molecular weight polymers where the molecular weight typically exceeds $1\times10^6$ daltons. It is a high molecular weight polysaccharide made up of blocks of mannose and glucose residues that are connected by β-(1-4) glycosidic bonds with usually a ratio of 1.6:1.0 mannose to glucose residues within the polysaccharides in a random order. This linear structure is generally interspersed with branches on C3 of the sugar residues, connected via a by β-(1-3) linkage, at approximately every tenth hexose unit, with an esterified acetyl group at approximately every nine-nineteenth residue, contributing to a high solubility of the glucomannan in water.

Also preferred are glucomannans that have similar physiochemical properties to konjac glucomannan, as described herein. The specific ratio of mannose to glucose ratio in konjac glucomannan enables it to interact with carrageenan and xanthan gum. Thus, the glucomannan (eg konjac glucomannan) preferably has a mannose to glucose ratio of between 1.6:1 and 3:2 (eg 1.6:1) and/or branching on C3 of the sugar residues at approximately every tenth hexose unit, and/or an esterified acetyl group at approximately every 9-19$^{th}$ residue. The acetyl groups are bound every 9-19 units, which can result in the high solubility of konjac glucomannan in water. In general, the degree of polymerisation affects the strength of fibre. Konjac glucomanan generally has a degree of polymerisation of larger than 6000, and so glucomannans that have a degree of polymerisation of larger than 6000 are preferred. The molecular chain composition and acetylation rates of konjac glucomannan can be described or tested using gas chromatography (GC), high performance liquid chromatography (HPLC), fourier transformed infrared spectroscopy (FTIR) and nuclear magnetic resonance (NMR). It is known in the art that the viscosity and solubility of konjac glucomannan can be hindered by the addition of competing solutes, low-molecular-weight ingredients such as partially hydrolysed guar gum or maltodextrin, branched dextrins and salts, or by the use of alcohols, such as ethanol or isopropyl alcohol, that will eventually precipitate the glucomannan chains from solution.

Glucomannan is commercially available from a number of sources in a crude form, for example konjac flour. Commercially available glucomannan can be divided into two types, ie the konjac flour/konjac gum (E425i) and the konjac glucomannan (E425ii). Preferably, purified glucomannan with at least 80% purity is used in the present invention. Purified grade glucomannan could be commercially obtained under the trade names of konjac gum E425ii, glucomannan KJ22, KS30, Konjac A, BJ-A1, BJ-C1 or others.

Methods of extracting glucomannan from a source (for example, from konjac) are well known to those skilled in art. An exemplary method of obtaining glucomannan is outlined below. For example, konjac glucomannan can be manufactured through two main continuous preparations: (a) Preparation of konjac root/tuber raw powder followed by (b) Preparation of purified konjac tuber extract/powder. In (a), the konjac tuber is merely subjected to washing, cutting, drying and milling. After the raw konjac tuber powder is obtained, konjac glucomannan is extracted through processes that include steeping and a series of milling and separation. In this extraction process, approximately 98% food grade alcohol diluting to 40-50% by water is used as an extraction solvent. This is a crucial purification and extraction process that removes the unwanted starch and other alkaloids that may present harmful effect. A quality control check is generally performed after vacuum drying and sieving of the glucomannan powder. At the end of processing, sample of purified glucomannan are collected for viscosity and characterisation (such as purity) analysis to assure compliance with established specification parameters. A similar process can be used to obtain glucomannan from other natural sources, adapted as appropriate.

Preferably, the glucomannan is provided in a purified form, for example having at least 80%, 85%, 90% or 95% purity.

Carrageenans are a family of linear sulphated polysaccharides that are typically extracted from various red algae (Rhodophyta), such as Gigartinaceae, Solieriaceae, Hypneaceae or Furcellariaceae. For example, the carrageenan can be derived from *Kappaphycus alvarezii* or *Eucheuma denticulatum*. The polysaccharides are composed of repeating galactose units and 3,6-anhydrogalactose (3,6-AG), both sulphated and nonsulphated, joined by alternating alpha-1,3 and beta-1,4 linkages. They have an average molecule weight of above 100,000 daltons. However, a person skilled in the art will also appreciate that carrageenan can be obtained from various sources apart from the types of red algae as set forth in this description.

In one embodiment, the carrageenan is one that has been obtained from a seaweed such as a red algae including any of Gigartinaceae, Solieriaceae, Hypneaceae, and Furcellariaceae.

Methods of extracting carrageenan from an appropriate source (for example, from a seaweed such as a red algae) are well known to those skilled in art. Outlined below is an exemplary method of producing refined grade of carrageenan.

For example, carrageenan may be extracted from a seaweed such as a red algae into an aqueous solution containing an alkali, such as sodium- or potassium-hydroxide. The alkali removes some of the sulphate groups from the molecules and increases the formation of 3,6-anhydrogalactose, which leads to a better gel strength. Centrifugation and/or filtration is applied to remove any non-dissolved material therefrom. The carrageenan is then recovered from the resulting carrageenan solution (eg by precipitation with potassium chloride or alcohol), and then is typically dried. The product is known as refined carrageenan.

Several members of the carrageenan family are known, differing in their amounts of sulphate ester and/or other substituent groups, including, kappa-carrageenan or iota-carrageenan. The types of carrageenan may be distinguished, in part, by their degree and position of sulphation, the proportion of 3,6-anhydrogalactose, as well as the red algae from which they are obtained. Carrageenans also vary in molecular weight, cation content and cation type. The gel strength of carrageenan should be more than 1000 g/cm$^2$. The gel strength can be measured by any commercially available texture analyser.

In a particular embodiment, the carrageen is kappa-carrageenan. Thus, the carrageenan may be kappa-carrageenan that has been extracted from a seaweed such as a red algae including any of Gigartinaceae, Solieriaceae, Hypneaceae, and Furcellariaceae. For example, kappa-carrageenan can be derived from *Kappaphycus alvarezii*, which is of the Solieriaceae family. For example, the kappa-carrageenan used in the present invention can be commercially obtained under the trade name of Gelcarin™, GRINDSTED™, Satiagel™, BLG Kappa refined carrageenan, or Lautagel R.

Kappa-carrageenan typically contains ester sulphate and in particular around 22% ester sulphate and 36% 3,6- anhydrogalactose. It can form thermo-reversible brittle gel, and has been used widely as a gelling agent in the food industry since the 1950s.

Preferably, the kappa-carrageenan is sodium salt kappa-carrageenan. Sodium salt kappa-carrageenan has an affinity to monovalent/divalent cations (and, in particular, potassium ions), which stabilises the junction zones within characteristically firm and brittle gels. The interactions between sodium salt kappa-carrageenan and the monovalent/divalent cations lead to the gel being less brittle.

Also preferred are carrageenans that have similar physiochemical properties to kappa-carrageenan. Hence, the carrageenan may be one that contains ester sulphate and 3,6-anhydrogalactose, such as around 22% ester sulphate and 36% 3,6-anhydrogalactose. The carrageenan is also preferably in a sodium salt form. These characteristics of kappa-carrageenan can be identified based on the identification test parameters stated in the European Pharmacopoeia (8$^{th}$ edition) or British Pharmacopoeia (2010, ISBN: 9780113228287).

Xanthan gum is a high molecular weight exocellular heteropolysaccharide produced by the *Xanthomonas* bacterium. It is a water soluble polysaccharide composed of a beta-(1,4)-linked D-glucose backbone with trisaccharide chains on alternating anhydroglucose units. Each side chain comprises a glucuronic acid unit between two mannose units. At most of the terminals, mannose units are pyruvylated, and the mannose unit adjacent to the main chain typically carries a 6-linked acetyl ester. Xanthan gums with varying degrees of acetylation and/or pyruvylation are included within the scope of the invention. Also included are non-acetylated and non-pyruvylated-xanthan gum variants which can be produced by fermentation of mutant strains of *Xanthomonas* or produced via chemical or enzymatic processes performed on conventional xanthan gum (ie xanthan gum with naturally occurring acetylation and/or pyruvylation). Xanthan gum is generally stable to acids, alkaline and enzymes, and it shows synergistic swelling and viscosity effect when combined with glucomannan and kappa-carrageenan.

Preferably, the xanthan gum has a purity of at least 91% such as in the range of 91.0-117% or 91.0-108% (eg in the range of 91%-100%); and has a viscosity of at least 1000 mPa·s. The purity of xanthan gum can be tested according to purity method of assay stated on JECFA monograph of xanthan gum, whereas the viscosity can be tested according to the viscosity method stated on USP, BP or EP monograph of xanthan gum using a viscometer. It will be appreciated that the purity values may be measured values that include the margin of error in whatever testing method is used.

It is also preferred if the degree of pyruvylation is at least 1.5%. The degree of pyruvylation can be determined by measuring the pyruvic acid content of xanthan gum, using the method stated on Food Chemical Codex (FCC), the Joint FAO/WHO Expert Committee on Food Additives (JECFA), United States Pharmacopoeia (USP), British Pharmacopoeia (BP), or European Pharmacopoeia (EP) monograph of xanthan gum.

Xanthan gum produces a highly viscous solution at low concentrations. Unlike other gums, such as carboxymethyl cellulose (CMC), carrageenan, pectin, and others, the viscosity of xanthan gum solution is remarkably stable under a wide pH range of 2-12 over a long period of time.

Xanthan gum can be obtained by a well-known fermentation process via precipitation with isopropanol from a fermented broth of a xanthan gum-producing bacterium, such as *Xanthomonas campestris, Xanthomonas carotate, Xanthomonas incanae, Xanthomonas begoniae, Xanthomonas papavericola, Xanthomonas translucens, Xanthomonas vasculorum*, and *Xanthomonas hederae*. All these species can produce a xanthan gum fermented broth; however, it is preferred if the xanthan gum for use in the present invention is prepared from *Xanthomonas campestris*. Xantham gum can be commercially obtained under the trade name of XANTURAL®, KELTROL®, GRINDSTED™ Xanthan, Satiaxane™, Ziboxan™, FuFeng xanthan gum.

Xanthan gum is readily available as a sodium, potassium or calcium salt, or as mixtures of sodium, potassium or calcium salts, and at varying levels of pyruvate and/or acetylation.

By monovalent or divalent cation salt, we include the meaning of any monovalent or any divalent salt known to a person skilled in the art. The monovalent or divalent salt can be a potassium, rubidium, caesium, ammonium, sodium, lithium, calcium, barium, magnesium or zinc salt. Preferably, the monovalent or divalent salt used in the present invention is a soluble salt that is capable of providing a cation, and most preferably is a potassium salt. Preferably, the potassium salt is a water-soluble potassium salt. Examples include potassium bicarbonate, potassium chloride, potassium acetate and potassium citrate. In a preferred embodiment, the potassium salt is potassium bicarbonate. The salt is preferably one that plays a role in the gelation of kappa-carrageenan.

The compositions of the invention comprise effective amounts of glucomannan, carrageenan, xanthan gum and a potassium salt. By an "effective amount" we include an amount that produces the desired viscosity and swelling capability (such as that exemplified in Example 3). Effective amounts of glucomannan, carrageenan, xanthan gum, and a monovalent or divalent salt (such as potassium salt) are proportionate amounts of each of these components that produce the desired viscosity and swelling capability. Effective amounts of the composition can also refer to the amounts of the composition that produce the desired viscosity and swelling capability under a pH condition resembling the pH of a stomach and/or a pH condition resembling the pH of an intestine. For example, the desired viscosity and swelling capability of the composition may be produced under a pH condition of a pH of less than 3.5 (eg 1.2) and/or under a pH condition of 6-7.5 (eg 6.8). It will be appreciated that these pH conditions are ones which, respectively, resemble the pH of a stomach and intestine, and so the composition may comprise effective amounts of the listed components that produce the cited swelling indexes under conditions (eg pH conditions) resembling stomach conditions and/or intestine conditions. Effective amounts of the composition can also refer to the amounts of the composition that produce the desired viscosity and swelling capability when ingested into a subject.

Another advantageous property of the composition of the invention is its swelling capability. This can be assessed by way of a swelling index, measured in ml/g, which corresponds to a volume of gel formed following incubation of the composition in a liquid divided by the initial weight of the composition prior to incubation. Thus, in a preferred embodiment, the composition swells under pH condition resembling the pH of a stomach and/or a pH condition resembling the pH of an intestine. For example, the composition may swell under a pH condition of a pH of less than 3.5 (eg 1.2) and/or a pH condition of 6-7.5 (eg 6.8). It will be appreciated that these pH conditions are ones which, respectively, resemble the pH of a stomach and intestine, and so the composition may comprise effective amounts of the listed components that enable the composition to swell under conditions (eg pH conditions) resembling stomach condition and/or intestine conditions. By swelling under gastric and/or intestinal conditions we include the meaning of the volume of the composition increasing when exposed to such conditions.

The swelling capability of the composition under pH condition resembling the pH of a stomach or a pH condition resembling the pH of an intestine can be simulated by preparing a simulated gastric fluid or a simulated intestinal fluid. An example of the preparation of the simulated gastric fluid and the method of the swelling test is further detailed in Example 3.

In another preferred embodiment, the composition gels under gastric and intestinal conditions.

It is to be noted that the swelling capability of the present composition in gastric, ie acidic conditions, is more crucial as it achieves its intended effects through forming a viscous, thick and indigestible gel structure that increases the volume of gastric content and slows down the food leaving from the stomach to duodenum, thereby inducing the feeling of satiety or fullness.

The proportions of glucomannan, carrageenan, xanthan gum and a monovalent or divalent cation salt may be about 30-50% w/w glucomannan (eg about 30%, 31%, 32%, 33%, 34%, 35%, 36%, 37%, 38%, 39%, 40%, 41%, 42%, 43%, 44%, 45%, 46%, 47%, 48%, 49%, or 50% w/w); about 15-25% w/w carrageenan (eg about 15%, 16%, 17%, 18%, 19%, 20%, 21%, 22%, 23%, 24%, or 25% w/w); about 10-25% w/w xanthan gum (eg about 10%, 11%, 12%, 13%, 14%, 15%, 16%, 17%, 18%, 19%, 20%, 21%, 22%, 23%, 24%, or 25%); and about 10-30% w/w potassium salt (eg about 10%, 11%, 12%, 13%, 14%, 15%, 16%, 17%, 18%, 19%, 20%, 21%, 22%, 23%, 24%, 25%, 26%, 27%, 28%, 29%, or 30% w/w). Preferably, the glucomannan is konjac glucomannan, the carrageenan is kappa-carrageenan, and the monovalent or divalent cation salt is a potassium salt, such as potassium bicarbonate.

In a preferred embodiment, the composition comprises glucomannan (eg konjac glucomannan) in an amount of 30-50% w/w by weight of the composition.

In a preferred embodiment, the composition comprises carrageenan (eg kappa-carrageenan) in an amount of 15-25% w/w by weight of the composition.

In a preferred embodiment, the composition comprises xanthan gum in an amount of 10-25% w/w by weight of the composition.

In a preferred embodiment, the composition comprises a monovalent or divalent cation salt in an amount of 10-30% w/w by weight of the composition.

In a preferred embodiment, the composition comprises: 40% w/w glucomannan; 24% w/w carrageenan; 16% w/w xanthan gum; and 20% w/w potassium salt. Preferably, the glucomannan is konjac glucomannan, the carrageenan is kappa-carrageenan, and the monovalent or divalent cation salt is a potassium salt, such as potassium bicarbonate.

As explained further below, the composition of the invention is typically prepared in a form suitable for oral use, such as in a capsule form. An exemplary formulation comprises about 625 mg of the composition. Thus, the composition may comprise about 220-280 mg glucomannan (eg about 220 mg, 230 mg, 240 mg, 250 mg, 260 mg, 270 mg, or 280 mg); about 140-160 mg carrageenan (eg about 140 mg, 150 mg or 160 mg); about 90-110 mg xanthan gum (eg about 90 mg, 100 mg or 110 mg); and about 90-160 mg potassium salt (eg about 90 mg, 100 mg, 110 mg, 120 mg, 130 mg, 140 mg, 150 mg or 160 mg). In a preferred embodiment, the composition comprises 250 mg glucomannan; 150 mg carrageenan; 100 mg xanthan gum; and 125 mg potassium salt. Preferably, the glucomannan is konjac glucomannan, the carrageenan is kappa-carrageenan, and the monovalent or divalent cation salt is a potassium salt, such as potassium bicarbonate.

Whilst it is possible for the agent of the invention to be administered alone, it may be desirable to present it as a pharmaceutical formulation, together with one or more acceptable excipient/diluent/carrier(s). The excipient/diluent/carrier(s) must be "acceptable" in the sense of being compatible with the therapeutic agent and not deleterious to the recipients thereof. Thus, it is appreciated that the invention provides a pharmaceutical composition comprising the composition according to the first aspect of the invention, and a pharmaceutically acceptable carrier, excipient or diluent. Preferably, an excipient/diluent/carrier suitable for solid dosage form is used.

Where appropriate, the compositions of the invention are conveniently presented in unit dosage form and may be prepared by any of the methods well known in the art of pharmacy and/or in the manufacture of oral compositions. Such methods include the step of bringing into association the active ingredient (eg the composition) with the carrier which constitutes one or more accessory ingredients. In general, the formulations are prepared by uniformly and intimately bringing into association the active ingredient (eg the composition) with finely divided solid carriers or liquid carriers or both, and then, if necessary, shaping the product.

Formulations in accordance with the present invention suitable for oral administration may be presented as discrete units such as capsules, cachets or tablets, each containing a predetermined amount of the composition; as a powder or granules; as a solution or a suspension in an aqueous liquid or a non-aqueous liquid; or as an oil-in-water liquid emulsion or a water-in-oil liquid emulsion. The composition may also be presented as a bolus, electuary or paste. Of course, it will be appreciated that the formulation is one that can be safely administered to the patent, for example without the risk of choking. In accordance with the preferred embodiment of the present invention, the dosage form of the composition is capsule.

Formulations suitable for topical administration in the mouth include lozenges comprising the active ingredient (eg the composition) in a flavoured basis, usually sucrose and acacia or tragacanth; capsules or pastilles comprising the active ingredient (eg the composition) in an inert basis such as gelatin and glycerin, or sucrose and acacia.

It should be understood that in addition to the ingredients particularly mentioned above the formulations of this invention may include other agents conventional in the art having regard to the type of formulation in question, for example those suitable for oral administration may include flavouring agents.

In a preferred embodiment, the composition of the invention is in the form of a capsule (eg gelatin capsule), tablet, powder, syrup, solution, suspension, sachet or shake.

For oral consumption, it will be appreciated that the compositions may be added to a food or beverage. For example, a powdered form of the composition may be mixed with a liquid (eg an indigestible liquid) to form an aqueous beverage or mixed with cookie batter prior to baking. Again, however, it will be appreciated that the composition should not alter the safety of the food or beverage product.

Hence, the invention also provides a food or beverage product comprising an effective amount of the composition of the invention comprising glucomannan, carrageenan, xanthum gum and a potassium salt. Preferences for the glucomannan, carrageenan, xanthum gum and a potassium salt, and proportions therefore, include those described above. The food products may be dietary supplements or meal replacements. Examples include shakes or smoothies. Typically, the food products or beverage products of the invention comprise from about 2% to about 50% w/w (eg from about 2% to about 40%, or from about 2% to about 30%, or from about 2% to about 20%, or from about 2% to about 10%) of a composition comprising glucomannan, carrageenan, xanthan gum and a potassium salt. Similarly, the food products or beverage products typically comprise between about 2 grams and about 20 grams of the composition per serving (such as between about 3 and about 10 grams, or about 4 and about 8 grams per serving).

The food products or beverage products may further comprise additional components such as proteins or amino acids, carbohydrates, lipids, vitamins, minerals and co-factors, natural or artificial flavours, dyes or other colouring additives, and preservatives.

In some embodiments, the composition (or food product or beverage product incorporating the composition) further comprises one or more therapeutic agents, such as: absorption-altering agents including lipase inhibitor, eg orlistat and cetilistat, alpha amylase inhibitors, eg white kidney bean extract, and alpha glucosidase inhibitors, eg acarbose and tannins; appetite altering agents including pharmaceutical agents, eg sibutramine, phentermine, diethylpropion, rimonabant, benzphetamine, and nutraceutical agent, eg potato extract; metabolism-altering agents such as monoxidine, green tea extract, garcinia cambogia extract, citrus aurantum extract; cholesterol-lowering agents including statins, eg simvastatin, atorvastatin, lovastatin, pravastatin and rosuvastatin, fibrates, eg gemfibrosil, bezafibrate, fenofibrate or ciprofibrate, bile acid sequestrants eg, colestipol, cholestyramine and nutraceuticals, eg plant sterol; or any combination thereof.

Although the composition of the invention may be provided in the form of a capsule or in some other ready made up form suitable for oral administration, it will be appreciated that the individual glucomannan, carrageenan, xanthan gum, and monovalent or divalent cation salt, such as potassium salt, may be mixed just prior to administration.

A second aspect of the invention provides a composition of the first aspect of the invention of the invention, for use in medicine.

A third aspect of the invention provides a method for preparing a composition of the first aspect of the invention or a food or beverage product comprising such a composition. For example, the method may comprise combining effective amounts of glucomannan, carrageenan, xanthan gum and monovalent or divalent cation salt to have a swelling index of at least 120 ml/g under pH condition resembling the pH of a stomach and/or to have a swelling index of at least 250 ml/g under pH condition resembling the pH of an intestine. For example, the method may have the swelling index at least of 120 ml/g or of at least 250 ml/g under a pH condition of a pH of less than 3.5 (eg 1.2) and/or a pH condition of 6-7.5 (eg 6.8). It will be appreciated that these pH conditions are ones which, respectively, resemble the pH of a stomach and intestine, and so the method may comprise combining effective amounts of the listed components to swell under conditions (eg pH conditions) resembling stomach condition and/or intestine conditions. The swelling index is typically measured after at least 1, 2, 3 or 4 hours after exposure to the stated conditions, and preferably around 4 hours after exposure to the stated conditions. Preferences for the glucomannan, carrageenan, xanthan gum and potassium salt, as well as their relative proportions, include those described above in relation to the first aspect of the invention.

In a further embodiment, the method of preparing a food or beverage product comprising the composition of the first aspect of the invention, comprises adding an effective amount of glucomannan, carrageenan, xanthan gum and potassium to a food or beverage product.

As mentioned above, composition of the invention forms a viscous, thick and indigestible gel structure in either the acidic stomach and/or alkaline intestine. This physical structure is believed to increase the gastric distension and to delay gastric emptying, thereby inducing the feeling of satiety or fullness. The formation of a viscous gel matrix is also believed to trap nutrients and food, leading to a flattened and prolonged glucose response after meals, and thus reduce hunger feelings and food cravings. Hence, the composition of the invention has utility in general weight management.

Accordingly, a fourth aspect of the invention provides a method of promoting satiety, reducing appetite, managing weight, combating obesity, managing blood glucose level, combating diabetes, lowering blood cholesterol, or combating metabolic syndrome, the method comprising administering to a subject a composition comprising: glucomannan; carrageenan; xanthan gum; and a potassium salt.

Obesity is a medical condition in which excess body fat has accumulated to the extent that it may have an adverse effect on health, leading to reduced life expectancy and/or increased health problems. Subjects are considered obese when their body mass index (BMI), a measurement obtained by dividing a person's weight in kilograms by the square of the person's height in meters, is 30 kg/m$^2$ or greater.

Obesity increases the likelihood of various diseases, particularly heart disease, type 2 diabetes, obstructive sleep apnea, certain types of cancer, and osteoarthritis.

BMI is calculated by dividing the subject's mass by the square of his or her height, typically expressed in metric units:

$$BMI = \text{weight in kilograms}/(\text{height in meters})^2$$

The most commonly used definitions, established by the World Health Organization (WHO) in 1997 and published in 2000, provide the values listed in the table below.

| BMI | Classification |
| --- | --- |
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Metabolic syndrome is a combination of medical disorders that, when occurring together, increase the risk of a subject developing diseases such as cardiovascular disease and diabetes. Metabolic syndrome is also known as metabolic syndrome X, cardiometabolic syndrome, syndrome X, insulin resistance syndrome, Reaven's syndrome (named for Gerald Reaven), and CHAOS (in Australia).

There are a number of different definitions for metabolic syndrome, as follows:

The International Diabetes Federation consensus worldwide definition of metabolic syndrome (2006) is: central obesity (defined as waist circumference with ethnicity-specific values) and any two of the following:

raised triglycerides: >150 mg/dL (1.7 mmol/L), or specific treatment for this lipid abnormality reduced HDL cholesterol: <40 mg/dL (1.03 mmol/L) in males, <50 mg/dL (1.29 mmol/L) in females, or specific treatment for this lipid abnormality raised blood pressure (BP): systolic BP>130 or diastolic BP>85 mm Hg, or treatment of previously diagnosed hypertension raised fasting plasma glucose (FPG): >100 mg/dL (5.6 mmol/L), or previously diagnosed type 2 diabetes If a subject's BMI is greater than 30 kg/m$^2$, central obesity can be assumed and waist circumference does not need to be measured.

The World Health Organization criteria (1999) require the presence of any one of diabetes mellitus, impaired glucose tolerance, impaired fasting glucose or insulin resistance, and two of the following:

blood pressure: ≥140/90 mm Hg dyslipidemia: triglycerides (TG): ≥1.695 mmol/L and high-density lipoprotein cholesterol (HDL-C)≤0.9 mmol/L (male), ≤1.0 mmol/L (female)

central obesity: waist:hip ratio>0.90 (male); >0.85 (female), or body mass index>30 kg/m$^2$ microalbuminuria: urinary albumin excretion ratio 20 µg/min or albumin:creatinine ratio 30 mg/g The European Group for the Study of Insulin Resistance (1999) requires insulin resistance defined as the top 25% of the fasting insulin values among nondiabetic individuals and any two or more of the following:

central obesity: waist circumference ≥94 cm (male), ≥80 cm (female)

dyslipidemia: TG≥2.0 mmol/L and/or HDL-C<1.0 mmol/L or treated for dyslipidemia hypertension: blood pressure≥140/90 mmHg or antihypertensive medication fasting plasma glucose≥6.1 mmol/L The US National Cholesterol Education Program Adult Treatment Panel III (2001) requires at least three of the following:

central obesity: waist circumference≥102 cm or 40 inches (male), 88 cm or 36 inches(female)

dyslipidemia: TG≥1.7 mmol/L (150 mg/di)

dyslipidemia: HDL-C<40 mg/dL (male), <50 mg/dL (female)

blood pressure≥130/85 mm Hg, or treated for hypertension fasting plasma glucose≥6.1 mmol/L (110 mg/dl)

In certain embodiments, metabolic syndrome is as defined according to the International Diabetes Federation consensus worldwide definition of metabolic syndrome (2006).

In certain embodiments, metabolic syndrome is as defined according to The World Health Organization criteria (1999).

In certain embodiments, metabolic syndrome is as defined according to The European Group for the Study of Insulin Resistance (1999).

In certain embodiments, metabolic syndrome is as defined according to The US National Cholesterol Education Program Adult Treatment Panel III (2001).

The invention thus includes a composition comprising: glucomannan; carrageenan; xanthan gum; and a potassium salt for use in promoting satiety, reducing appetite, managing weight, combating obesity, managing blood glucose level, combating diabetes, lowering blood cholesterol, or combating metabolic syndrome.

Similarly, the invention also includes the use of a composition comprising: glucomannan; carrageenan; xanthan gum; and a potassium salt in the manufacture of a medicament for promoting satiety, reducing appetite, managing weight, combating obesity, managing blood glucose level, combating diabetes, lowering blood cholesterol, or combating metabolic syndrome.

Preferences for the composition include those described above in relation to the first aspect of the invention. Thus, it will be appreciated that the method of the fifth aspect of the invention includes administering the composition of the first aspect of the invention to a subject. It is preferred if the glucomannan is konjac glucomannan, the carrageenan is kappa-carrageenan, and the potassium salt is potassium bicarbonate. It is also preferred that the composition comprises 40% w/w glucomannan; 24% w/w carrageenan; 16% w/w xanthan gum; and 20% w/w potassium salt.

In certain embodiments, the subject is a human, a primate, bovine, ovine, equine, porcine, avian, rodent (such as mouse or rat), feline, or canine. Preferably, the subject is a human.

The composition may be administered before a meal (such as at least about 120, 110, 100, 90, 80, 70, 60, 50, 40, 30, 20, or 10 minutes before a meal), during a meal (including as part of the meal), after a meal (such as at least about 10, 20, 30, 40, 50, 60, 70, 80, 90, 100, 110, or 120 minutes after a meal) or any time in between two meals. Preferably, the composition is taken anytime before or after a meal.

Preferably, the composition is administered to the subject between 30 minutes and 60 minutes before having a meal, for example about 30 minutes, 40 minutes, 50 minutes or 60 minutes before having a meal.

It will be appreciated that the composition may be administered to the subject once a day, twice a day, three times a day or more. Preferably, the composition is administered three times a day, and most preferably, between 30 minutes and 60 minutes before having a meal.

Suitable dosage amounts may contain a predetermined quantity of active composition calculated to produce the desired therapeutic effect in association with the required diluent and/or carrier and/or excipient. A therapeutically effective amount can be determined by the medical worker skilled in the art based on patient characteristics, such as age, weight, sex, condition, complications, other diseases, etc., as is well known in the art.

In a particular embodiment, the composition is administered in the form of a capsule containing 250 mg glucomannan (eg konjac glucomannan), 150 mg carrageenan (eg kappa-carrageenan), 100 mg xanthan gum and 125 mg potassium salt (eg potassium bicarbonate). Preferably two such capsules are ingested with around 250 ml water, before a meal, for example between 30 minutes and 60 minutes before a meal, optionally three times a day.

In an embodiment of the fifth aspect of the invention, the method or use, may also involve administering one or more therapeutic agents to the subject, such as such as absorption-altering agents; appetite-altering agents; metabolism-altering agents;

cholesterol-lowering agents; or any combination thereof, as set forth in the preceding description.

It is appreciated that the composition of the invention will usually be administered separately from the one or more therapeutic agents. In such an embodiment, the composition and the additional one or more therapeutic agents may be administered sequentially, or they may be administered substantially simultaneously, either through distinct routes of administration or the same route of administration (eg oral). However, it is appreciated that in some cases, a combined formulation could be useful. Thus, in certain embodiments, the composition, pharmaceutical composition, of food product or beverage product of the invention may further comprise the one or more additional therapeutic agents.

Thus, the invention includes one or more therapeutic agents (such as an anti-obesity agent, an anti-obesity neutraceutical, or an appetite suppressant, including any one or more of the specific examples listed above) for use in promoting satiety, reducing appetite, managing weight, combating obesity, managing blood glucose level, combating diabetes, lowering blood cholesterol, or combating metabolic syndrome of a subject, wherein the subject is administered a composition according to the first aspect of the invention. Similarly, the invention includes a composition according to the first aspect of the invention for use in promoting satiety, reducing appetite, managing weight, combating obesity, managing blood glucose level, combating diabetes, lowering blood cholesterol, or combating metabolic syndrome of a subject, wherein the subject is administered one or more therapeutic agents (such as an anti-obesity agent, an anti-obesity neutraceutical, or an appetite suppressant, including any one or more of the specific examples listed above).

EXAMPLES

Example 1 Exemplary Composition of Invention

1. Product Description

IQP-AK-102 is a product in capsule form, containing the following active ingredients:
a) 40% w/w konjac glucomannan
b) 24% w/w kappa-carrageenan
c) 16% w/w xanthan gum
d) 20% w/w potassium bicarbonate The composition achieves its intended action by promoting the sensation of satiety/fullness, which subsequently reduces the hunger sensation and food craving.

The four active ingredients in the composition: purified konjac glucomannan, kappa-carrageenan, xanthan gum and potassium bicarbonate act synergistically to form a viscous, thick and indigestible gel structure in either acidic stomach or alkaline intestinal condition. This physical structure increases the gastric distension and delays gastric emptying, thereby inducing the feeling of satiety or fullness. The formation of viscous gel matrix also traps the nutrient and food, leading to a flattened and prolonged glucose response after meal and thus reduces hunger feelings and food cravings. Hence, the composition is indicated for treatment and prevention of obesity and for general weight management.

2. Exemplary Applications/Uses 2.1 Indications

The composition achieves its intended action by promoting the sensation of satiety/fullness, which subsequently reduces the hunger sensation and food craving. The composition is for the treatment and prevention of obesity and for general weight management.

2.2 Recommended Dosage

Each capsule of the composition contains 250 mg of purified konjac glucomannan, 150 mg of kappa-carrageenan, 100 mg of xanthan gum and 125 mg potassium bicarbonate. The recommended dosage of the composition is two capsules to be ingested with a full glass of water (approximately 250 ml), 30 minutes to 60 minutes before main meals (three meals/day).

Example 2: Swelling Index Test

The measurement of swelling index is performed in an in vitro system mimicking the in vivo gastric condition, according to modified European Pharmacopeia swelling index method (Ph Eur. 2.8.4). The in vitro gastric condition can be simulated by using simulated gastric fluid without enzymes, made by dissolving 2.0 g of NaCl in 7 ml of concentrated HCl followed by dilution with distilled water to 1000 ml (see USP).

A measuring cylinder (test model) is added with 1 ml of absolute alcohol, 0.05 g of test material and 25 ml of simulated gastric fluid solution. The test model is shaken and incubated. Two distinct layers will be observed, and the volume of the gel layer demonstrated the swelling capability of the test material.

The swelling index can be obtained by the volume in milliliters occupied by the known weight of test material, after incubating in room temperature for four (4) hours, ie:

Calculate swelling index (ml/g)=recorded volume/weight of sample, for the three test models.

The relative swelling capability (as percentage) can be obtained by the ratio of the swelling volume of tested sample to the composition, ie:

Calculate relative swelling capability=(swelling volume of tested sample/swelling volume of the composition)×100%, for the three test models.

Table 1 shows the swelling index data of the composition of IQP-AK-102 in simulated gastric fluid and simulated intestinal fluid, respectively resembling the stomach and intestinal conditions.

TABLE 1

| Test Material | Test Condition | Swelling Index (ml/g) | Fold** |
|---|---|---|---|
| IQP-AK-102 | pH 1.2 | >120 | >80 |
|  | pH 6.8 | >250 | >150 |

Figure 1:
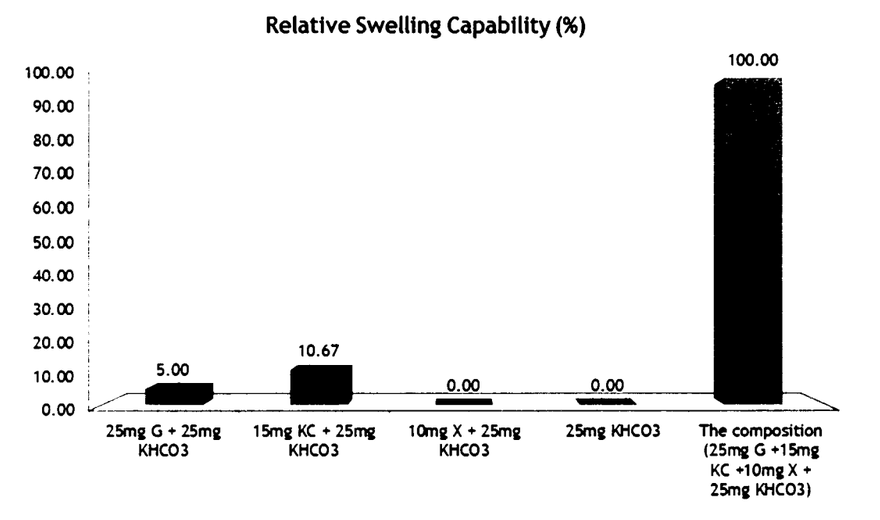
FIG. 1 is a graph showing relative swelling capability (%) of exemplary compositions as described in one of the preferred embodiments of the present invention. Relative swelling capability=(swelling volume of tested sample/swelling volume of IQP-AK-102×100%).

**Fold = volume of gel formed/volume of test material
~Volume of powder = mass of test material/bulk density of test material Example 3: Relative Swelling Capability of Exemplary Composition of Invention Table 2 shows the average swelling volume (ml) for the different test samples. A relative swelling capability (%) was shown in FIG. 1.

TABLE 2

| Test Sample | Avg. Swelling Volume (ml) |
|---|---|
| 25 mg glucomannan (G) + 25 mg KHCO3 | 1.25 |
| 15 mg kappa-carrageenan (KC) + 25 mg KHCO3 | 2.67 |
| 10 mg xanthan gum (X) + 25 mg KHCO3 | 0.00 |
| 25 mg potassium bicarbonate (KHCO3) | 0.00 |
| IQP-AK-102 (25 mg G + 15 mg KC + 10 mg X + 25 mg KHCO3) | 25.00 |

The invention claimed is:

1. A method of promoting satiety, reducing appetite, managing weight, combating obesity, managing blood glucose level, combating diabetes, lowering blood cholesterol, or combating metabolic syndrome, the method comprising administering to a subject a composition comprising glucomannan; carrageenan; xanthan gum; and a monovalent or divalent cation salt, wherein the glucomannan is present in an amount of 30-50% w/w by weight of the composition.

2. The method according to claim 1, wherein the glucomannan is konjac glucomannan.

3. The method according to claim 1, wherein the composition further comprises a therapeutic agent.

4. The method according to claim 3, wherein the therapeutic agent is an absorption altering agent, an appetite altering agent, a metabolism altering agent, a cholesterol lowering agent or any combination thereof.

5. The method according to claim 1, wherein the carrageenan is derived from a red algae.

6. The method according to claim 1, wherein the red algae is selected from the group consisting of: Gigartinaceae; Solieriaceae; Hypneaceae; and Furcellariaceae.

7. The method according to claim 1, wherein the carrageenan is kappa-carrageenan or iota-carrageenan.

8. The method according to claim 1, wherein the monovalent or divalent cation salt is a water-soluble potassium salt.

9. The method according to claim 1, wherein the potassium salt is selected from the group consisting of: potassium bicarbonate; potassium chloride; potassium acetate; potassium phosphate; and potassium citrate.

10. The method according to claim 1, wherein the carrageenan is present in an amount of 15-25% w/w by weight of the composition.

11. The method according to claim 1, wherein the xanthan gum is present in an amount of 10-25% w/w by weight of the composition.

12. The method according to claim 1, wherein the potassium salt is present in an amount of 10-30% w/w by weight of the composition.

13. The method according to claim 1, wherein the composition comprises 15-25% w/w carrageenan; 10-25% w/w xanthan gum; and 10-30% w/w monovalent or divalent cation salt.

14. The method according to claim 13, wherein the composition comprises 40% w/w glucomannan; 24% w/w carrageenan; 16% w/w xanthan gum; and 20% w/w monovalent or divalent cation salt.

15. The method according to claim 1, wherein the composition comprises 220-280 mg glucomannan; 140-160 mg carrageenan; 90-110 mg xanthan gum; and 90-160 mg monovalent or divalent cation salt.

16. The method according to claim 1, wherein the composition comprises 250 mg glucomannan; 150 mg carrageenan; 100 mg xanthan gum; and 125 mg monovalent or divalent cation salt.

17. The method according to claim 1, wherein the composition has a swelling index of at least 120 ml/g under a pH condition resembling the pH of a stomach.

18. The method according to claim 1, wherein the composition has a swelling index of at least 250 mg/g under a pH condition resembling the pH of an intestine.

19. The method according to claim 1, wherein the swelling volume of the composition is increased by at least 80 fold.

20. The method according to claim 1, wherein the composition swells under a pH condition resembling the pH of a stomach or the pH of an intestine.

21. The method according to claim 1, wherein the composition increases viscosity under pH condition resembling the pH of a stomach or the pH of an intestine.

22. The method according to claim 1, wherein the composition gels under pH condition resembling the pH of a stomach or the pH of an intestine.

23. The method according to claim 1, wherein the composition is in the form of a capsule, tablet, powder, syrup, solution, suspension, sachet or shake.

24. The method according to claim 1, wherein the composition is a food product or beverage product.

25. The method according to claim 1, wherein the composition further comprises a pharmaceutically acceptable carrier and/or excipient and/or diluent.

26. The method according to claim 24, wherein the food beverage of product is a dietary supplement, a meal replacement, or a food additive.

* * * * *